United States Patent [19]

Bricker et al.

[11] Patent Number: 4,717,779

[45] Date of Patent: * Jan. 5, 1988

[54] DEHYDROGENATION OF DEHYDROGENATABLE HYDROCARBONS

[75] Inventors: Jeffery C. Bricker; Tamotsu Imai; David E. Mackowiak, all of Mt. Prospect, Ill.

[73] Assignee: UOP Inc., Des Plaines, Ill.

[*] Notice: The portion of the term of this patent subsequent to Mar. 6, 2001 has been disclaimed.

[21] Appl. No.: 893,754

[22] Filed: Aug. 6, 1986

Related U.S. Application Data

[63] Continuation-in-part of Ser. No. 774,841, Sep. 11, 1985, abandoned, which is a continuation-in-part of Ser. No. 708,833, Mar. 6, 1985, abandoned.

[51] Int. Cl.$^4$ ................................................ C07C 5/40
[52] U.S. Cl. ...................... 585/443; 585/319; 585/440; 585/444; 585/654; 585/658; 585/659; 585/660; 585/661; 585/662
[58] Field of Search ............... 585/441, 442, 443, 444, 585/445, 655, 656, 657, 658, 660, 661, 662, 663, 319

[56] References Cited

U.S. PATENT DOCUMENTS

| | | | |
|---|---|---|---|
| 3,966,895 | 6/1976 | Wilhelm | 585/442 |
| 4,418,237 | 11/1983 | Imai | 585/443 |
| 4,435,607 | 3/1984 | Imai | 585/443 |
| 4,565,898 | 1/1986 | O'Hara et al. | 585/441 |

Primary Examiner—Asok Pal
Attorney, Agent, or Firm—Thomas K. McBride; John F. Spears, Jr.; Raymond H. Nelson

[57] ABSTRACT

Dehydrogenatable hydrocarbons may be subjected to a dehydrogenation reaction in which the hydrocarbons are treated with a dehydrogenation catalyst comprising a modified iron catalyst in the presence of steam in a multicatalyst bed system. The reaction mixture containing unconverted hydrocarbons, dehydrogenated hydrocarbons, hydrogen and steam is then contacted with an oxidation catalyst whereby hydrogen is selectively oxidized. The selective oxidation catalyst which is used will comprise a noble metal of Group VIII of the Periodic Table, a metal of Group IVA and, if so desired, a metal of Group IA or IIA composited on a porous inorganic support. The inorganic support will comprise an alumina precursor which possesses and ABD less than about 0.6 g/cc, a pore volume greater than about 0.5 cc/g, and a pore distribution such that between 10% and 70% of the pore volume is present as pores whose diameters are greater than about 300 Angstroms. After peptizing and calcination at a temperature of about 900° to about 1500° C., the resulting alumina will possess an ABD in the range of from about 0.3 to about 1.1 g/cm, a pore volume greater than about 0.2 cc/g, a pore distribution such that more than 40% of the pore volume is present in pores greater than 1500 Angstroms, a piece density in the range of from about 0.3 to about 2.0 g/cc, and a particle size which possesses a diameter of at least 2 mm.

19 Claims, No Drawings

DEHYDROGENATION OF DEHYDROGENATABLE HYDROCARBONS

CROSS-REFERENCE TO RELATED APPLICATION

This application is a continuation-in-part of our copending application Ser. No 774,841 filed Sept. 11, 1985 now abandoned, which is a continuation-in-part of our copending application Ser. No. 708,833 filed Mar. 6, 1985, and now abandoned, all teachings of which are incorporated herein by reference thereto.

BACKGROUND OF THE INVENTION

It has been known in the prior art that unsaturated hydrocarbons may be obtained from the dehydrogenation of dehydrogenatable hydrocarbons. The dehydrogenation may be effected by subjecting the dehydrogenatable hydrocarbons to a dehydrogenation process at dehydrogenation conditions in the presence of certain catalytic compositions of matter which possess the ability to dehydrogenate said compounds with the resultant formation of olefinic hydrocarbons. The particular dehydrogenation catalysts which are employed are well known in the art and comprise such compounds as nickel composited on a solid support such as diatomaceous earth, kieselguhr, charcoal and iron composited on the same supports, etc.

Other dehydrogenation processes have employed, in addition to the dehydrogenation catalysts, an oxidation catalyst in the reaction process. The presence of the oxidation catalyst is necessitated by the fact that it is advantageous to oxidize the hydrogen which is produced by contact with an oxygen-containing gas in order to maintain the desired reaction temperature. For example, styrene, which is an important chemical compound utilized for the preparation of polystyrene, plastics, resins or synthetic elastomers such as styrene-butadiene rubber, etc., may be prepared from the dehydrogenation of ethylbenzene. The dehydrogenation of ethylbenzene into styrene, which is effected by treating ethylbenzene with steam in the presence of a modified iron catalyst, is endothermic in nature. The heat of reaction is about 30 Kcal per mole of ethylbenzene. Therefore, the temperature of the catalyst bed decreases significantly during the progress of the reaction in a commercial adiabatic reactor resulting in limitation of ethylbenzene conversion to a low level. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level, but also the selectivity for styrene, since at equilibrium conditions, only undesirable side reactions continue to take place. Therefore, it is necessary to maintain the desired temperature level in order to provide a high equilibrium conversion level and a high reaction rate. In the conventional process, the maintenance of temperature is attained by reheating the product stream with the addition of superheated steam between dehydrogenation catalyst beds using a multicatalyst bed reactor system. However, consumption of the additional superheated steam is considerably high and makes the dehydrogenation process costly. Accordingly, significant process economic improvements over the conventional ethylbenzene dehydrogenation processes can be achieved if the reaction temperature is somehow maintained while eliminating or reducing the additional superheated steam. One method of providing for the maintenance of the reaction temperature is to introduce oxygen into the reaction mixture by way of oxygen or an oxygen-containing gas such as air which will burn the hydrogen formed during the dehydrogenation reaction, this combustion resulting in an exothermic reaction which will provide the necessary amount of heat and, in addition, will shift the equilibrium toward production of styrene since the hydrogen formed in the dehydrogenation is consumed. Consequently, a higher conversion and high styrene selectivity are achievable.

The combustion of hydrogen with the oxygen in the oxygen-containing gas requires the presence of an oxidation catalyst. There are some key requirements for the oxidation catalyst to be useable for such a purpose. The most important catalytic property required is good catalytic stability since the oxidation catalyst must survive under very severe reaction conditions, namely at about 6000° to 650° C. in the presence of steam. Under such conditions, porous inorganic materials such as aluminas, silicas and zeolites cannot maintain their pore structures for a long period of time, resulting in the permanent damage of catalysts prepared using such materials as supports, e.g., platinum supported on a porous high surface area alumina, silica, or zeolite. Secondly, the oxidation catalyst must be very active to achieve complete conversion of oxygen to avoid poisoning of iron-based dehydrogenation catalysts which are sensitively oxidized with oxygen to lose their dehydrogenation activities. Thirdly, the oxidation catalyst must be selective for oxidation of hydrogen. Otherwise, ethylbenzene and styrene are consumed to lower the efficiency of styrene production.

Various U.S. patents have described types of oxidation catalysts which may be employed in this process. For example, U.S. Pat. No. 3,437,703 describes a catalytic dehydrogenation process which employs, as a dehydrogenation catalyst, a composition known in the trade as Shell-105 which consists of from 87% to 90% ferric oxide, 2% to 3% chromium oxide, and from 8% to 10% of potassium oxide. In addition, another dehydrogenation catalyst which is employed comprises a mixture of nickel, calcium, chromic oxide, graphite with a major portion of a phosphate species. In addition to these dehydrogenation catalysts, the reaction also employs a catalyst for the oxidation step of the process comprising platinum or palladium in elemental form or as a soluble salt. Another U.S. Pat. No. 3,380,931, also discloses an oxidation catalyst which may be used in the oxidative dehydrogenation of compounds such as ethylbenzene to form styrene comprising an oxide of bismuth and an oxide of a metal of Group VIB of the Periodic Table such as molybdenum oxide, tungsten oxide or chromium oxide. In addition, the patent also states that minor amounts of arsenic may also be present in the catalytic composite as well as other metals or metalloids such as lead, silver, tin, manganese, phosphorus, silicon, boron and sulfur.

U.S. Pat. No. 3,855,330 discloses a method for the production of styrene in which ethylbenzene is treated in the vapor state by passage over a dehydrogenation catalyst and an oxidation catalyst while introducing oxygen into the reaction medium. The dehydrogenation catalysts which are employed are those which have been set forth in various prior U.S. patents and which may be similar in nature to the dehydrogenation catalysts previously discussed. The types of oxidation catalysts which may be employed will include platinum or palladium catalysts which are composited on alumina or molecular sieves zeolite-type which have been charged with ferrous, heavy or noble metals. The patent lists the types of catalysts which are employed including copper or various zeolites, platinum on alumina, platinum on spinel, platinum and sodium on zeolites, platinum, sodium and potassium on zeolites, etc.

U.S. Pat. No. 3,670,044 discloses a method for dehydrogenating cycloalkane, arylalkane and alkanes in the presence of gaseous hydrogen or mixture of gaseous hydrogen and gaseous oxygen using a catalyst composition comprising a Group VIII metal or a mixture of a Group VIII metal and a Group IVA metal deposited on a support comprising a Group II aluminate spinel. It is noted that the patentee teaches that added hydrogen is used in connection with the oxygen, and that when only oxygen is used, the conversion and selectivity are generally low. The addition of hydrogen is believed to be a significant disadvantage in the dehydrogenation process inasmuch as the equilibrium conversion is lowered. This is in contradistinction to the process of the present invention wherein the dehydrogenation process, prior to the oxidation step, is not effected in the presence of any added hydrogen. As will hereinafter be shown in greater detail, the present process results in the selective oxidation of hydrogen with a concomitantly lower selectivity to carbon monoxide and carbon dioxide. In addition, the patentee teaches the use of one catalyst for both dehydrogenation and oxidation which is in contrast to the separate dehydrogenation and oxidation catalysts which are used in the present process.

In addition to the aforementioned U.S. patents, another patent, namely U.S. Pat. No. 4,435,607 also discloses a method for the dehydrogenation of dehydrogenatable hydrocarbons utilizing a two-step process which includes dehydrogenation followed by a selective oxidation process. The catalyst which is employed for the selective oxidation will comprise a noble metal of Group VIII, a metal of Group IVA and, if so desired, a metal of Group IA or IIA of the Periodic Table composited on a highly porous inorganic support. The catalyst base which is used to prepare the oxidation catalyst in this patent was prepared from particles which were relatively small in size.

The patent utilizes as a support for the catalytic metals an alumina which does not possess the properties which are possessed by the precursor or the calcined alumina of the present invention and is totally silent with regard to pore distribution and density of the support. In other words, the patent does not teach the desirability of utilizing as an alumina support for the oxidation catalyst of the process of the present invention a support which possesses the requisite pore size distribution.

However, as will hereinafter be shown in greater detail, we have now discovered that by utilizing, as a support for the metallic portions of the catalyst, a particular type of alumina precursor which possesses certain physical properties, it is possible to obtain a superior catalyst with relation to stability and conversion over those catalysts which have been used in prior processes.

BRIEF SUMMARY OF THE INVENTION

This invention relates to a process for the dehydrogenation of dehydrogenatable hydrocarbons. More specifically, the invention is concerned with a process for the dehydrogenation of a dehydrogenatable hydrocarbon in which the hydrocarbon which is to undergo treatment is subjected to a dehydrogenation step in the presence of a dehydrogenation catalyst. This dehydrogenation step is followed by a selective oxidation step in which the product mixture which results from the aforementioned dehydrogenation step is treated in the presence of certain catalytic compositions of matter which are hereinafter set forth in greater detail in such a manner whereby the hydrogen which is present and which has resulted from the dehydrogenation step is selectively oxidized with a concomitant minimum oxidation of the hydrocarbons. By utilizing the particular support for the selective oxidation catalyst, it is possible to obtain the desired dehydrogenated hydrocarbons in a relativly high yield as well as maintaining the stability and activity of the catalyst to a greater degree than has heretofore been experienced. By maintaining the aforementioned stability and activity, it is possible to obviate the necessity for relatively frequent changes of the catalyst or, in the alternative, regenerating the catalyst, thereby adding to the commercial attractiveness and economical feasibility of the dehydrogenation process.

It is therefore an object of this invention to provide a process for the dehydrogenation of dehydrogenatable hydrocarbons.

A further object of this invention is to provide a catalyst for the selective oxidation step of the process whereby hydrogen which is formed during the dehydrogenation process will be selectively oxidized to the substantial exclusion of the oxidation of the hydrocarbons.

In one aspect an embodiment of this invention resides in a process for the dehydrogenation of dehydrogenatable hydrocarbons with separate and intermediate selective oxidation of hydrogen which comprises: (a) contacting said hydrocarbons with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of unconverted hydrocarbons, dehydrogenated hydrocarbons, hydrogen and steam; (b) removing said first-reaction dehydrogenation zone effluent from said first-reaction dehydrogenation zone; (c) passing said removed first-reaction dehydrogenation zone effluent of step (b) to a second-reaction oxidation zone, which is separate and discrete from said first-reaction dehydrogenation zone; (d) contacting said first-reaction dehydrogenation zone effluent in said second-reaction oxidation zone with an oxygen-containing gas to selectively oxidize said hydrogen within said first-reaction zone effluent to the substantial exclusion of oxidation of said unconverted and dehydrogenated hydrocarbons in the presence of an oxidation catalyst consisting essentially of a Group VIII noble metal, a Group IVA metal, and a Group IA or IIA metal composited on an alumina support at oxidation conditions wherein said exothermic selective oxidation of said hydrogen provides additional heat and thereby raises the temperature of said unconverted and dehydrogenated hydrocarbons; (e) withdrawing said unconverted and dehydrogenated hydrocarbons from said second-reaction oxidation zone having an increased temperature with respect to the temperature of said first-reaction dehydrogenation zone effluent; (f) passing said removed second-reaction oxidation zone product stream of step (e) to a third-reaction dehydrogenation zone containing a dehydrogenation catalyst comprising an alkaline metal-promoted iron compound at dehydrogenation conditions to produce dehydrogenated hydrocarbons; and (g) withdrawing and recovering said dehydrogenated hydrocarbons, the improvement which comprises utilizing as said support precursor for said oxidation catalyst an alumina which possesses an Apparent Bulk Density less than about 0.6 g/cc, a pore volume greater than about 0.5 cc/g, a pore distribution such that between 10% and 70% of the pore volume is present in pores greater than 300 Angstroms in diameter, and which catalyst support, after peptizing and calcination thereof, possesses an Apparent Bulk Density in the range of from about 0.3 to about 1.1 g/cc, a pore volume greater than about 0.2 cc/g, a pore distribution such that more than 40% of the pore volume is present in pores greater than about 1500 Angstroms, a piece density in the range of from about 0.3 to about 2.0 g/cc, and a particle size which possesses a diameter of at least 2 mm.

A specific embodiment of this invention is found in a process for the dehydrogenation of ethylbenzene which comprises contacting said ethylbenzene with a dehydrogenation catalyst comprising an alkaline metal modified iron catalyst at a temperature in the range of from about 500° C. to about 700° C. and a pressure in the range of from about 0.1 to about 10 atmospheres in the presence of steam, thereafter contacting the resultant mixture of unconverted ethylbenzene, styrene, hydrogen and steam with air at a temperature in the range of from about 500° to about 700° C. and a pressure in the range of from about 0.1 to about 10 atmospheres in the presence of a catalyst comprising a mixture of platinum, tin and lithium composited on an alumina support which has been obtained from an alumina precursor which possesses an Apparent Bulk Density less than about 0.6 g/cc, a pore volume greater than about 0.5 cc/g, a pore distribution such that between 10% and 70% of the total pore volume is present in pores greater than about 300 Angstroms in diameter and which catalyst support, after peptizing and calcination, possess an Apparent Bulk Density in the range of from about 0.3 to about 1.1 g/cc, a pore volume greater than about 0.2 cc/g, a pore distribution such that more than 40% of the pore volume is present in pores greater than about 1500 Angstroms in diameter, a piece density in a range of from about 0.3 to about 2.0 g/cc, a surface area of from 1 to 40 m²/g and a diameter of at least 2 mm whereby hydrogen is selectively oxidized, and recovering the desired styrene after the final stage of dehydrogenation.

Other objects and embodiments will be found in the following detailed description of the invention.

DETAILED DESCRIPTION OF THE INVENTION

As hereinbefore set forth, the present invention is concerned with a dehydrogenation process for the dehydrogenation of dehydrogenatable hydrocarbons which involves the use, in one step of the process, of a selective oxidation catalyst which will provide improved stability and effectiveness of the active elements as well as eliminating some disadvantages which have been present with prior catalytic compositions of matter used in the same process.

The particle size of the selective oxidation catalyst which is utilized to selectively oxidize hydrogen is very critical in nature. The importance of the particle size is due to the pressure drop which is associated with catalyst particles which are relatively small in size. For example, when utilizing processes such as a stacked bed setup, in which dehydrogenation catalyst and oxidation catalyst are present in two distinct layers or beds an undesirable pressure drop may be created by the presence of the oxidation catalyst. In many dehydrogenation reactions the conversion of the dehydrogenatable hydrocarbon is relatively sensitive to the pressures which are employed to effect the conversion. For example in the conversion of ethylbenzene to styrene, as the pressure which is employed increases, the equilibrium conversion level decreases in a significant manner. In view of the effect of pressure discussed above, it has now been discovered that a critical parameter present in the selective oxidation catalyst is the size of the particle of the support upon which the metallic components of the system are composited. The size of the particle must be large enough so that the pressure drop in the process which is usually associated with the catalyst does not limit the conversion of the dehydrogenatable hydrocarbon to the dehydrogenated hydrocarbon. In this respect, as we have now discovered and as will be hereinafter shown in greater detail, it is possible to obtain a catalyst support which comprises particles of relatively large size which will permit the obtention of a catalyst system for use in a selective oxidation process whereby extremely high conversions of the starting materials and a concurrent high selective oxidation of hydrogen, which is a by-product of the dehydrogenation process, may be obtained.

In the present process, a dehydrogenatable hydrocarbon of the type hereinafter set forth in greater detail is contacted with a dehydrogenation catalyst in the presence of steam in a multicatalyst bed system. Inasmuch as the dehydrogenation of the hydrocarbon is endothermic in nature, it is necessary to provide an additional amount of heat before the product enters the next catalyst bed in order to provide a high equilibrium conversion as well as a high reaction rate. One method of effecting this increase in the desired temperature is to provide an internal catalytic combustion of the hydrogen which is produced during the dehydrogenation reaction in order to reheat the product to the desired level. By effecting a selective oxidation of the hydrogen, it is possible to avoid the use of superheated steam or other outside sources of heat. This selective oxidation of hydrogen with the resultant composition thereof is effected by utilizing a selective oxidation catalyst of the type hereinafter set forth in greater detail, the selective oxidation catalyst maintaining its stability and activity for a considerable length of time.

The process of the present invention may be effected by utilizing an apparatus in which the dehydrogenation catalyst and the oxidation catalyst, both of the type hereinafter set forth in greater detail, are loaded in the apparatus in alternate layers. The number of alternate layers of dehydrogenation catalyst and selective oxidation catalyst may vary according to the size or type of apparatus which is employed, the number of alternate layers ranging from three to about nine. As will hereinafter be shown, the dehydrogenation catalyst and the oxidation catalyst are different in nature. Examples of dehydrogenation catalysts which may be employed will comprise an alkaline earth metal-promoted iron compound. The term "alkaline metal" as used in the present specification and appended claims will refer to metals of Groups IA and IIA of the Periodic Table which include lithium, sodium, potassium, rubidium, cesium, beryllium, magnesium, calcium, strontium and barium. In addition, the promoted iron compound catalyst will, in the preferred embodiment of the invention, also include a compound containing a metal of Groups IVB, VB and VIB of the Periodic Table. For example, a typical dehydrogenation catalyst which may be employed in the process of this invention will consist essentially of about 85% by weight of ferric oxide, 12% by weight of potassium hydroxide, 2% by weight of chromia and 1% by weight of sodium hydroxide. Another typical dehydrogenation catalyst which may be used comprises 90% by weight of ferric oxide, 4% by weight of chromia and 6% by weight of potassium carbonate. In addition to these catalysts, other well-known dehydrogenation catalysts which may be utilized will include those comprising ferric oxide, potassium oxide, as well as other metal oxides and/or sulfides of metals of Groups IA, IIA, IVB, VB and VIB of the Periodic Table including those of calcium, lithium, strontium, magnesium, beryllium, zirconium, tungsten, molybdenum, hafnium, vanadium, copper, chromium and mixtures of two or more oxides such as chromia-alumina, chromia-titania, alumina-vanadia and the like.

The dehydrogenation of a dehydrogenatable hydrocarbon such as, for example, ethylbenzene, is effected by contacting the dehydrogenatable hydrocarbon and steam, in the absence of any added hydrogen, with the aforesaid catalyst at dehydrogenation conditions which are in the range of from about 500° to about 700° C. and at a reaction pressure in the range of from about 0.1 to about 10 atmospheres; the exact dehydrogenation conditions are, however, a function of the particular dehydrogenatable hydrocarbon undergoing dehydrogenation. Other reaction conditions will include a Liquid Hourly Space Velocity based on the hydrocarbon charge of from about 0.1 to about 10 hrs-1 and steam to hydrocarbon weight ratios ranging from about 1:1 to about 40:1. The number of dehydrogenation zones of the catalyst beds may vary from 1 to about 5 in number and typically may comprise three reaction zones; however, the number of zones is not critical to the invention.

After contacting the dehydrogenation catalyst with the steam and hydrocarbon, the resulting mixture comprising unconverted hydrocarbon, dehydrogenated hydrocarbon, steam and hydrogen which has passed through the catalyst bed is contacted in a separate zone with the selective oxidative catalytic composition of the type hereinafter set forth in greater detail. In addition, oxygen-containing gas is introduced into the reactor, preferably at a point adjacent to the oxidation catalyst bed. Examples of oxygen-containing gases which may be utilized to effect the selective oxidation of the hydrogen which is present will include air, oxygen, air or oxygen diluted with other gases such as steam, carbon dioxide and inert gases such as nitrogen, argon, helium, etc. The amount of oxygen which is introduced to contact the product stream may range from about 0.1:1 to about 2:1 moles of oxygen per mole of hydrogen contained in the product stream. In this particular reaction zone, the product stream, which comprises unreacted dehydrogenatable hydrocarbon, dehydrogenated hydrocarbon, hydrogen and steam, undergoes a selective oxidation in contact with oxygen and the oxidation catalyst whereby hydrogen is selectively oxidized to water with a minimal amount of reaction of oxygen with the hydrocarbons, either unconverted hydrocarbon or dehydrogenated hydrocarbon.

After passage through the zone containing the oxidation catalyst, the mixture may then be passed through a second dehydrogenation zone containing a dehydrogenation catalyst of the type hereinbefore set forth for further dehydrogenation, the process being completed through the plurality of zones followed by withdrawal of the product stream and separation of the unconverted hydrocarbon from the desired dehydrogenated product.

It is contemplated that the dehydrogenation process for the dehydrogenation of dehydrogenable hydrocarbons utilizing the oxidative catalytic compositions of matter of the present invention will be applicable to a wide variety of dehydrogenatable hydrocarbons. Examples of hydrocarbons which are susceptible to a dehydrogenation process utilizing the catalysts of the present invention will include lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isopropyltoluene, ethylnaphthalene, propylnapththalene, isopropylnaphthalene, diethylnaphthalene, etc., paraffins such as ethane, propane, n-butane, isobutane, n-pentane, isopentane, n-hexane, n-heptane, n-octane, n-nonane, n-decane, and branched chain isomers thereof, cycloparaffins such as cyclobutane, cyclopentane, cyclohexane, methylcyclopentane, methylcyclohexane, ethylcyclopentane, olefins such as ethylene, propylene, 1-butene, 2-butene, 1-pentene, 2-pentene, 1-hexene, 2-hexene, 3-hexene, and branched chain derivatives thereof, etc.

The selective oxidation step of the process utilizes, as hereinbefore set forth, the hydrogen which has been produced in the dehydrogenation step of the process to supply heat to the inlet of the next dehydrogenation catalyst bed. Inasmuch as temperatures which are utilized in the process may be as high as 650° C. in the presence of steam, the operating conditions in which the oxidation catalyst must function are severe in nature. In order for the oxidation catalyst to remain stable and minimize the carbon formation thereon, the catalyst support must be calcined at a relatively high temperature in order to decrease the surface area, this decrease in surface area contributing to the stability of the catalyst. Conventional oxidation catalysts utilizing a porous support such as alumina which had been calcined at relatively low temperatures, i.e., below about 900° C. or lower, lose surface area at a rapid rate and form excessive carbon on the surface thereof, thus resulting in a deactivation of the catalyst.

An effective oxidation catalyst which may be used in the dehydrogenation and selective oxidation process of the present invention comprises a noble metal of Group VIII of the Periodic Table such as platinum along with a Group IVA metal of the Periodic Table such as tin and, if so desired, a metal selected from Group IA and IIA of the Periodic Table composited on a solid porous inorganic oxide support. A particularly effective support which contributes to the stability and effectiveness of the catalyst comprises an alumina. We have now discovered that certain aluminas may be selected as the precursor for the suppodrt which will, after peptizing of the precursor and calcination, provide a support for the catalytic metals of the composite, the final composite possessing the necessary stability to effectively operate as an efficient catalyst over a relatively long period of time. The alumina support will be derived from various types of aluminas such as, for example, boehmite, pseudoboehmite, gibbsite, etc. which possess certain desirable properties or characteristics. The alumina must be a low density compound in which the Apparent Bulk Density (ABD) is preferably less than about 0.6 g/cc, the pore volume greater than about 0.5 cc/g, the pore distribution such that between 10% and 70%, and preferably between about 10% and 50%, of the total pore volume is present in pores greater than 300 Angstroms in diameter, and a surface area of from about 100 to aboubt 400 m$^2$/g. By utilizing such a precursor, it is possible after peptizing of the precursor and calcination, to obtain a finished catalyst support which will provide the enhanced stability which is desired to be present in the final catalyst composite. The calcination of the support is effected at a temperature within the range of from about 900° to about 1500° C. prior to impregnation of the metals thereon. If so desired, the calcination of this support may be effected in a dry atmosphere, preferably at a temperature in the range of from about 1100° to about 1500° C. or the calcination may be effected in a hydrous atmosphere such as that provided by steam, the temperatures preferably in the range of from about 900° to about 1200° C. The calcination of the support within these temperature ranges will be effected over a period of time which may range from about 0.5 to about 30 hours or more in duration and it is to be understood that the particular temperature which is selected for the calcination of the support will influence or direct the time frame during which the calcination takes place. It has been found that a particularly effective type of alumina source which may be in the form of pellets, spheres, powder, slurry, etc. and which will provide desired catalyst support comprises a low density alumina of the type hereinbefore set forth.

As will hereinafter be shown in greater detail, it has now been discovered that an alumina precursor known as Kaiser boehmite alumina will provide the desired catalyst base in contrast to other aluminas such as a Catapal boehmite alumina.

The alumina support which is recovered from the calcination step will, in the preferred embodiment of the invention, also possess certain desirable characteristics or properties. For example, the ABD of the finished support will preferably be in a range of from about 0.3 to about 1.1 g/cc, the pore volume greater than about 0.2 cc/g, the surface area in a range of from about 1 to about 40 m$^2$/g, the piece density in a range of from about 0.3 to about 2.0 g/cc, and a pore distribution such that more than 40% and preferably up to about 95% of the pore volume is present in pores greater than about 1500 Angstroms in diameter. The particle size of the alumina support which is obtained will be relatively large (e.g., at least about 2.0 mm in diameter). For example, particles which may be obtained by extruding this material will possess diameters in a range of from about 2 to about 15 mm, preferably in a range of from about 2.0 to about 8 mm, and may have a length in a range of from about 2 to about 50 mm, preferably in a range of from about 4 to about 18 mm. If the alumina support is not extruded but obtained by other means such as oil drop methods, it is possible to obtain particles in the shape of spheres which possess diameters in the range of from about 2.0 mm to about 20 mm, and preferably in a range of from about 2.0 to about 10 mm. In addition, the alumina may be present as alpha-alumina or as a mixture of alpha-alumina and theta-alumina.

The final catalyst support which will be utilized to prepare a selective oxidation catalyst of the present invention must possess these desired characteristics or properties. Among the most important of the properties are pore volume, piece density and pore distribution. As was previously stated, the desired catalyst must possess a relatively large pore volume, that is, greater than about 0.2 cc/g with a correspondingly low piece density, that is, from about 0.3 to about 2.0 g/cc. In addition, by possessing a large proportion, that is, greater than about 40% and up to about 95% of pores possessing a diameter of at least 1500 Angstroms, it is possible to obtain the desired base. The aforementioned parameters are critical, especially for large supports which possess a diameter greater than 2 mm, due to the fact that the reaction rate is limited by the diffusion of the reactants into and out of the catalyst. A catalyst support which is relatively porous in nature has an increased effective catalytic metal due to a more effective diffusion of reactants into the particle. The effective catalytic metal is defined as the metal which is participating in the reaction, divided by the total catalytic metal present on the catalyst. By utilizing the particular catalyst base of the present invention, it is possible to obtain a support which possesses a much greater effective catalytic metal due to the favorable pore structure as represented by the pore volume of the catalyst support.

As will hereinafter be shown in greater detail, the use of a support possessing the properties and sizes will result in the obtention of a catalyst composite which will exhibit greater stability and selectivity as well as a lower pressure drop when employed in the selective oxidation process than will be found when utilizing catalyst supports which possess properties and particle sizes outside the range set forth for the low density alumina precursors.

As was hereinbefore set forth, the selective oxidation catalysts which are employed in the process of this invention will comprise a noble metal of Group VIII of the Periodic Table and a metal of Group IVA of the Periodic Table composited on a solid inorganic support which, prior to the compositing of the metals thereon, has been peptized and thereafter calcined at a temperature within the range herebefore discussed. In addition, if so desired, it is also contemplated within the scope of this invention that the catalyst will also contain a metal selected from Groups IA and IIA of the Periodic Table. Of the noble metals of Group VIII of the Periodic Table, platinum, palladium and rhodium comprise the preferred species, said metals being present in the final composite in an amount in the range of from about 0.01% to about 5% by weight. Of the metals of Group IVA of the Periodic Table, germanium, tin and lead comprise the preferred species, these metals also being present in the final catalyst composite in an amount in the range of from about 0.01% to about 5% by weight. The preferred species of metals of Group IA or IIA of the Periodic Table will include lithium, sodium, potassium, rubidium, cesium, beryllium, magnesium, calcium, barium, francium, and radium, the alkali metals or alkaline earth metals being present in an amount in the range of from about 0.01% to about 10% by weight of the catalyst composite.

The selective oxidation catalyst which utilizes, as the support for the metallic portion of the composite, an alumina which possesses the desired properties hereinbefore set forth, may be prepared in any suitable manner known in the art. For example, one type of preparation will comprise mpregnating a solid support previously described, and which may be in the form of beads, spheres, pellets, etc., with an aqueous or acidic solution of a Group VIII metal compound of the Periodic Table. The form in which the support is used may have been prepared by various methods such as particles prepared by oil dropping, extrusion, pelletizing and binding with certain binders. The aqueous solution of the noble metal-containing compound may be prepared from soluble salts of these metals, such as chloroplatinic acid, chloropalladic acid, rhodium chloride, platinum sulfate, palladium sulfate, etc. The solid support is impregnated with the solution for a period of time which is sufficient to allow the deposition of the desired amount of the noble metal on the solid support, that is, an amount sufficient so that the finished catalytic composition will contain from about 0.01% to about 5% by weight of the composite. After recovery of the impregnated solid support, the composite is then dried and calcined at a temperature in the range of from about 500° to about 600° C. or more in an air or air/steam atmosphere.

The thus formed composite containing a noble metal may then be further impregnated with an aqueous solution of a metal of Group IVA of the Periodic Table. In a similar manner to that hereinbefore described, the amount of soluble salts such as tin chloride, tin bromide, tin sulfate, lead chloride, lead persulfate, germanium chloride, etc. will be present in the solution sufficient so that the finished catalytic composition will contain the desired amount of metals. Again, the impregnation is allowed to proceed for a predetermined period of time following which the composite is recovered, dried and calcined. In the event that it is desired to have a metal of Group I or IIA of the Periodic Table present in the catalyst composite, the third step of the process is effected in a similar manner by subjecting the composite to an impregnation utilizing an aqueous solution containing the desired metal. Examples of salts of these metals which may be employed will include potassium chloride, potassium bromide, potassium iodide, potassium nitrate, potassium sulfate, potassium acetate, potassium propionate, rubidium chloride, rubidium bromide, rubidium iodide, rubidium nitrate, rubidium sulfate, rubidium acetate, rubidium propionate, cesium chloride, cesium bromide, cesium iodide, cesium nitrate, cesium sulfate, cesium acetate, cesium propionate, calcium chloride, barium chloride, barium bromide, barium iodide, barium nitrate, barium sulfate, barium acetate, barium propionate, etc. After allowing the impregnation to proceed for a period of time sufficient to permit the deposition of the desired amount of metal on the catalyst, the composite is recovered, dried and calcined at a temperature within the range hereinbefore set forth, and recovered.

It is also contemplated that the preparation of the selective oxidation catalyst may be prepared by coimpregnating the noble metal of Group VIII of the Periodic Table, the metal of Group IVA of the Periodic Table, and if so desired, the metal of Group IA or IIA of the Periodic Table on the solid support. When such a type of preparation is employed, the solid support, such as alumina, is impregnated with an aqueous solution containing salts of the noble metal and the Group IVA metal along with, if so desired, the alkali metal or alkaline earth metal in a manner similar to that hereinbefore set forth. After allowing the impregnation to proceed for a predetermined period of time, the composite is recovered, dried and calcined at a temperature within the range hereinbefore set forth in an air or air/steam atmosphere, following which it is recovered for use in the oxidation portion of the process of the present invention.

Some specific examples of selective oxidation catalytic compositions of matter which may be used in the process of the present invention comprise, as hereinbefore set forth, the noble metals of Group VIII, a metal of Group IA or IIA, a metal of Group IVA, composited on a theta or alpha-alumina possessing the aforementioned physical properties and which has been calcined at a temperature within the ranges hereinbefore set forth. These examples will include platinum, germanium and lithium composited on alumina, palladium, germanium and potassium composited on alumina, rhodium, germanium and potassium composited on alumina, platinum, tin and potassium composited on alumina, palladium, tin and potassium composited on alumina, rhodium, tin and potassium composited on alumina, platinum, germanium and cesium composited on alumina, palladium, germanium and cesium composited on alumina, rhodium, germanium and cesium composited on alumina, platinum, tin and cesium composited on alumina, palladium, tin and cesium composited on alumina, rhodium, tin and cesium composited on alumina, platinum, germanium and barium composited on alumina, palladium, germanium and barium composited on alumina, rhodium, germanium and barium composited on alumina, platinum, tin and barium composited on alumina, palladium, tin and barium composited on alumina, rhodium, tin and barium composited on alumina, platinum, lead and potassium composited on alumina, palladium, lead and potassium composited on alumina, rhodium, lead and potassium composited on alumina, etc. It is to be understood that the above-enumerated catalysts are only representative of the selective oxidation composites which may be used in the process of this invention, and that said invention is not necessarily limited thereto. By utilizing a selective oxidative catalytic composition of matter in a process which involves the dehydrogenation of dehydrogenatable hydrocarbons, it is possible to obtain a process which, in addition to obtaining a desirable and commercially attractive yield of dehydrogenation products, also permits the operation of the process in an economically viable manner due to the catalytic stability of the catalyst under the relatively harsh and stringent operating conditions such as high temperature and high concentration of steam at which the process is operated.

By utilizing the particular alumina support upon which the catalytic metals are impregnated, it is possible to obtain a catalyst which exhibits the desired characteristics of stability and activity which is in contradistinction to prior art types of oxidation catalysts which cannot produce the desired stability exhibited by the present catalysts, and therefore cannot survive in use for a long period of time. This relatively short life of a catalyst discourages the commercial use of such catalysts as unattractive due to the necessity of having to replace or regenerate the catalyst after a short interval of operating time has elapsed. In addition, the catalysts of the present invention also exhibit a definite activity for the selective oxidation of hydrogen rather than a tendency for the oxidation of the dehydrogenated products or unreacted hydrocarbons.

As a further advantage of utilizing the particular alumina precursor to form alumina supports, as was hereinbefore stated, the aforementioned supports will be obtained, after the calcination step, in particles which are relatively large in size. As was previously mentioned, the large size of the catalyst particles will be advantageous inasmuch as the pressure drop of the feedstock through the catalyst bed will be minimal, thus contributing to a hydrocarbon conversion which is greater than hydrocarbon conversions which had been obtained when using other catalytic systems.

The particular effectiveness of the catalyst of the present invention which has been prepared from a particular type of alumina boehmite which acts as a support will be hereinafter shown in greater detail in the examples. The catalyst of the present invention will exhibit an excellent stability in that it possesses the ability to maintain the maximum temperature of the reaction at a position which is near the inlet of the catalyst bed. The desired reaction, that is, the selective oxidation of hydrogen, is highly exothermic in nature and it is therefore an indication of a good catalyst that the maximum temperature is maintained near the inlet of the catalyst bed, thus indicating that the conversion of the hydrogen occurs at a time shortly after the product stream comprising unconverted hydrocarbons, dehydrogenated hydrocarbons, steam and hydrogen enters the catalyst bed. In addition, as will hereinafter be demonstrated, the catalyst of the present invention also possesses the ability to effect a relatively high conversion of oxygen as is evidenced by the absence of oxygen in the exit gas which is withdrawn from the reaction zone containing the selective oxidation catalyst.

The following examples are given for purposes of illustrating the selective oxidation catalyst of the present invention as well as to a process utilizing the selective oxidation catalyst in said process. However, it is to be understood that these examples are merely illustrative in nature and that the present process is not necessarily limited thereto.

EXAMPLE I

A selective oxidation catalyst of the present invention was prepared by adding 10.0 grams of concentrated nitric acid to 546.5 grams of water followed by the addition of 7.60 grams of tin chloride. The resulting solution was then added to 569.8 grams of Kaiser boehmite alumina which possessed the desired physical properties hereinbefore set forth, that is, an ABD of less than 0.6 g/cc, a pore volume of greater than 0.5 cc/g and a mean particle diameter of less than 40 microns. The resulting material was mixed for a period of five minutes and thereafter extruded through a die which possessed 5.0 mm diameter holes using a double auger extruder. The extrudates were then dried in an oven for two hours at a temperature of 95° C.

The extrudates in an amount of 226.4 grams were placed in a quartz tube and calcined at a temperature of 350° C. in a flowing air atmosphere for a total time of 1.0 hours. The temperature was then increased to 600° C. while maintaining an air flow of 0.5 liters per minute, and after reaching this temperature the extrudate was calcined for an additional period of three hours in a flowing air atmosphere. At the end of this period of time, the extrudates were cooled to room temperature. To effect the high temperature calcination, 154.05 grams (418 cc) of precalcined extrudates were loaded into a ceramic tray and heated to a temperature of 1230° C. over a period of eight hours. Upon reaching this temperature, the material was calcined for a period of three hours and thereafter slowly cooled to room temperature over a period of eight hours. The final alumina support was analyzed and found to have an ABD of 0.59 g/cc, a pore volume of 0.668 cc/g, a piece density of 1.11 g/cc, a surface area of 10 m$^2$/g and the alumina was in the alpha phase. In addition, the extrudates possessed a diameter of 3.5 mm and were 6 mm in length.

The catalyst composite was then prepared by adding 6.98 grams of a chloroplatinic solution containing 2.52% by weight of platinum, 17.32 grams of lithium nitrate solution containing 1.02% by weight of lithium and 3.94 grams of concentrated nitric acid to 122 grams of water. The solution was mixed and then added to a glass steam-jacketed evaporator. The alumina support in an amount of 87.5 grams (150 cc) was added to the evaporator, the evaporator was rotated for 15 minutes at room temperature and thereafter steam was introduced into the steam jacket. The evaporator was then rotated for two hours in a stream of nitrogen which was introduced at a rate of one liter per minute and at the end of the two hour period, the introduction of steam was discontinued. The impregnated support was then dried in an oven for two hours at a temperature of 150° C. and calcined in a quartz tube. The calcination was effected by heating the tube from room temperature to 650° C. in the presence of a flowing air atmosphere which was introduced at a rate of about 0.5 liters per minute during a period of 2.0 hours. Upon reaching 650° C., the air stream at the same rate was bubbled through a water bubbler which had been heated to a temperature of 65° C., the calcination being effected for a period of two hours. At the end of the two hour period, the flow of air bypassed the water bubbler and calcination was effected for an additional period of one hour. At the end of this period, heating was discontinued and the catalyst composite was allowed to return to room temperature while maintaining the flowing air atmosphere.

EXAMPLE II:

Two additional catalyst composites were prepared in a similar manner. In one instance, the alumina precursor which was utilized as the support comprised a Catapal boehmite alumina which did not possess the same properties as did the Kaiser boehmite alumina. After calcination of the Catapal boehmite alumina, the alumina was found to have an ABD of 1.32 g/cc, a pore volume of 0.167 cc/g, a piece density of 2.42 g/cc, a surface area of 4 m$^2$/g, and the alumina was in the alpha phase. The extrudates which were obtained after calcination also were 3.5 mm in diameter and mm in length.

The second alumina support was prepared by admixing Kaiser boehmite alumina and Catapal boehmite alumina so that the finished support contained 25% Kaiser boehmite alumina and 75% Catapal boehmite alumina. After calcination in a manner similar to that hereinbefore set forth, the alumina support was found to possess an ABD of 1.06 g/cc, a pore volume of 0.258 cc/g, a piece density of 1.98 g/cc, a surface area of 6 m$^2$/g, and was in the alpha phase. The catalysts were analyzed for metal content and it was found that the catalyst prepared from 100% Kaiser boehmite alumina contained 0.156% by weight of platinum, 0.19% by weight of lithium and 1.0% by weight of tin. The catalyst which was prepared from the 100% Catapal boehmite alumina contained 0.164% by weight of platinum, 0.2% by weight of lithium and 1.0% by weight of tin. The mixed boehmite alumina catalyst contained 0.155% by weight of platinum, 0.19% by weight of lithium and 1.0% by weight of tin. The particle size of the extrudates were 3.5 mm in diameter and 6 mm in length.

EXAMPLE III

The catalysts which were prepared according to the above example were evaluated for oxygen conversion and selectivity for oxygen reacting with hydrogen to form water. The catalysts in an amount of 50 cc were loaded into a ⅞" inner diameter stainless steel reactor having a 10" long ½" diameter bore for the catalyst loading. The reactor was heated to an inlet temperature of 570° C. and a feedstock comprising a mixture of ethylbenzene, styrene, steam, hydrogen, oxygen and nitrogen which simulated a product stream at about a 60% ethylbenzene conversion from the second dehydrogenation catalyst bed of a three dehydrogenation catalyst bed reactor system having an oxidation catalyst bed positioned between the dehydrogenation catalyst beds was fed to the reactor. The feedstream was passed over the oxidation catalyst bed at the aforesaid inlet temperature and at a reactor outlet pressure of 0.7 atmospheres. The hydrocarbon feed was maintained at a Liquid Hourly Space Velocity of 10.3 hours$^{-1}$. The inlet feed ratio of the feed stream of ethylbenzene and styrene/$H_2O$/$H_2$/$O_2$/$N_2$ was 1.0/9/0.45/0.13/1. In addition, the air into the catalyst bed was controlled in order to maintain a maximum temperature of 630° C. in the reactor.

As an indication of the stability of the catalyst, measurements were taken to determine the position of the maximum temperature which was present in the bed of catalyst. As was previously set forth, the maximum catalyst temperature should be at a location near the inlet position of the catalyst. The desired reaction, which is the selective oxidation of hydrogen, is highly exothermic in nature and on feature which determines the stability and effectiveness of a catalyst composite is the position of the maximum catalyst temperature in the catalyst bed. In addition, another indication of catalyst stability is found in in the amount of oxygen which is present in the gas which exits from the reactor.

To summarize the differences between the desired catalyst base of the present invention as compared to the two other catalyst bases, the following tables graphically illustrate these differences:

TABLE I

| PROPERTIES OF BOEHMITE POWDERS | | |
|---|---|---|
| | Kaiser Boehmite | Catapal Alumina |
| Pore Volume cc/g | 0.92 | 0.42 |
| Pore Volume (> 300 A°) | 16% | 8% |
| total pore volume | | |
| ABD g/cc | 0.36 | 0.81 |

TABLE II

| | FINAL CATALYST SUPPORT PROPERTIES CATALYST | | |
|---|---|---|---|
| | A | B | C |
| | ALUMINA PRECURSOR | | |
| | Kaiser Boehmite | 25% Kaiser 75% Catapal | Catapal Boehmite |
| Pore volume cc/g | 0.668 | 0.258 | 0.167 |
| Piece density g/cc | 1.11 | 1.98 | 2.42 |
| ABD g/cc | 0.59 | 1.06 | 1.32 |
| Surface area m²/g | 10 | 6 | 4 |
| P.V. (> 1500 A°) | 66.6% | — | 2.6% |
| Total P.V. | | | |

EXAMPLE IV

The results of the selective oxidation tests which were performed accordingly to the method described in Example III above, are set forth in the tables below. In the tables, the catalyst of the present invention which is the catalyst composite prepared from the Kaiser boehmite alumina precursor which possesses the desired physical properties is designated as "A". The catalyst which was prepared from the alumina base comprising a mixture of 25% Kaiser boehmite alumina and 75% catapal boehmite laumina is designated as "B" and the catalyst which was prepared from 100% catapal boehmite alumina which does not possess the physical properties within the desired ranges is designated as "C".

TABLE III

| | Maximum Catalyst Temperature °C. | | |
|---|---|---|---|
| Hrs. On Stream | A | B | C |
| 6 | 630 | 630 | 628 |
| 12 | 630 | 630 | 628 |
| 18 | 632 | 629 | 630 |
| 30 | 629 | 630 | 627 |
| 42 | 630 | 631 | 628 |
| 54 | 629 | 630 | 627 |
| 66 | 630 | 630 | 627 |
| 78 | 630 | 629 | 627 |
| 90 | 631 | 629 | 626 |
| 114 | 630 | 629 | * |
| 126 | 630 | 629 | * |
| 138 | 630 | 629 | * |
| 150 | 630 | 628 | * |
| 162 | 630 | 628 | * |
| 174 | 629 | — | * |

*Additional heat had to be supplied to the catalyst bed by increasing the furnace temperature thereby artificially maintaining a maximum temperature in the bed of 630° C.

TABLE IV

| | Location of Maximum Temp. - Inches from Inlet of Catalyst Bed | | |
|---|---|---|---|
| Hrs. On Stream | A | B | C |
| 6 | 1.75 | 1.63 | 2.13 |
| 12 | 1.88 | 1.75 | 1.63 |
| 18 | 2.00 | 1.63 | 2.00 |
| 30 | 2.25 | 1.88 | 2.38 |
| 42 | 2.25 | 1.88 | 2.50 |
| 54 | 2.25 | 2.00 | 2.50 |
| 66 | 2.00 | 1.88 | 2.63 |
| 78 | 2.25 | 2.00 | 2.63 |
| 90 | 2.25 | 2.00 | 2.75 |
| 114 | 2.25 | 2.25 | 3.00 |
| 126 | 2.38 | 2.13 | 3.13 |
| 138 | 2.38 | 2.25 | 2.75 |
| 150 | 2.38 | 2.13 | 3.25 |
| 162 | 2.50 | 2.25 | 3.25 |
| 174 | 2.38 | — | 3.25 |

TABLE V

| | Composition of Exit Gas Oxygen + Argon (Mole Percent). | | |
|---|---|---|---|
| Hrs. On Stream | A | B | C |
| 6 | 0.5 | 0.5 | 0.5 |
| 12 | 0.5 | 0.5 | 0.5 |
| 18 | 0.4 | 1.3 | 0.5 |
| 30 | 0.4 | 0.6 | 0.5 |
| 42 | 0.4 | 0.5 | 0.5 |
| 54 | 0.5 | 0.5 | 0.6 |
| 66 | 0.5 | 0.5 | 0.6 |
| 78 | 0.5 | 0.6 | 0.5 |
| 90 | 0.4 | 2.4 | 0.5 |
| 114 | 0.4 | 0.5 | 0.6 |
| 126 | 0.6 | 0.8 | 0.5 |
| 138 | 0.4 | 0.5 | 0.4 |
| 150 | 0.4 | 0.5 | 0.5 |
| 162 | 0 4 | 0.6 | 0.5 |

TABLE V-continued

| | Composition of Exit Gas Oxygen + Argon (Mole Percent). | | |
|---|---|---|---|
| Hrs. On Stream | A | B | C |
| 174 | 0.6 | — | 0.5 |

It is apparent that the position of the maximum temperature in the catalyst bed differs when utilizing different catalyst bases, and in some instances will shift to a lower level in the bed. The catalyst base which was prepared from the catapal boehmite alumina which did not possess the desired physical properties showed a movement and lowering of the maximum temperature in the catalyst bed, thus indicating a lack of stability present in this catalyst which, over a longer period of time, would affect the effectiveness of the catalyst to selectively oxidize hydrogen to the exclusion of oxidation of the hydrocarbons. The catalyst prepared from the catalyst base of the present invention, that is, the Kaiser boehmite alumina which possessed the desired physical properties within the ranges hereinbefore set forth possesses the ability to reheat the product stream by oxidation of the hydrogen to provide the necessary heat for the subsequent dehydrogenation of any unconverted dehydrogenatable hydrocarbons which are present in said product stream. The differences in catalyst performance (A, B, and C) are magnified by consideration that as the density of the catalyst increases, the quantity of platinum loaded into the reactor increases proportionally. The density of catalysts B and C are substantially greater than A, such that the quantity of platinum loaded in the reactor for catalyst A is 0.046 grams, for catalyst B is 0.082 grams and for catalyst C is 0.108 grams. Thus, the quantity of platinum present in the reactor under testing of catalyst C (100% Catapal boehmite alumina) is over twice that present in the testing of catalyst A (100% Kaiser boehmite alumina). It is therefore readily apparent that a considerably lesser amount of noble metal such as platinum may be employed when using a catalyst base of the present invention as exemplified by catalyst A when compared to other catalyst bases as exemplified by catalysts B and C to effect better results in a selective oxidation process. This saving in the use of such noble metals will present a considerable economic advantage which will result in a viable commercial process. Therefore, there is *considerable* economic advantage to employing catalyst A, rather than catalysts B or C.

EXAMPLE V

To illustrate the effect of particle size on the pressure drop for the selective oxidation reaction two tests similar in nature to that described in the above examples were performed in which a feedstock similar in nature to that set forth in Example III above was passed over the catalyst of the present invention described in Example I as well as catalysts which were prepared according to the method set forth in U.S. Pat. No. 4,435,607. The size of the catayst particles prepared according to the process of the present invention comprised extrudates possessing a diameter of 3.5 mm and were 6 mm in length. In contrast to this, the catalyst which was supported by the method set forth in the aforementioned patent comprised spherical beads having a diameter of 1.4 mm. It was found that by passing the feedstream over the catalyst beds, a pressure drop as measured by lbs. per sq. in. per ft. when using the catalyst of the present invention, that is, using a Kaiser boehmite alumina as a precursor for the subsequently calcined support, was 0.65. In contrast to this, the pressure drop which was present when using the catalyst prepared according to the method set forth in the patent was double, that is, 1.3 lbs. per sq. in. per ft.

The pressure drop associated with the smaller catalyst particles will limit the extent of ethylbenzene conversion significantly compared with the larger catalyst particles, which will not create a pressure drop having significant effect on ethylbenzene conversion.

We claim as our invention:

1. In a process for the dehydrogenation of a dehydrogenatable hydrocarbon with separate and intermediate selective oxidation of hydrogen which comprises:
   (a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of uncovered hydrocarbon dehydrogenation hydrocarbons, hydrogen and steam;
   (b) removing said first-reaction dehydrogenation zone effluent from said first-reaction dehydrogenation zone;
   (c) passing said removed first-reaction dehydrogenation zone effluent of step (b) to a second-reaction oxidation zone, which is separate and discrete from said first-reaction dehydrogenation zone;
   (d) contacting said first-reaction dehydrogenation zone effluent in said second-reaction oxidation zone with an ozygen-containing gas to selectively oxidize said hydrogen within said first-reaction zone effluent to the substantial exclusion of oxidation of said unconverted and dehydrogenation hydrocarbons in the presence of an oxidation catalyst essentially of a Group VIII noble metal, a Group IV metal, and a Group IA or IIA metal composited on an alumina support at oxidation conditions wherein said exothermic selective oxidation of said hydrogen provides additional heat and thereby raises the temperature of said unconverted and dehydrogenated hydrocarbons;
   (e) withdrawing said uncoverted and dehydrogenated hydrocarbons from said second-reaction oxidation zone having an increased temperature with respect to the temperature of said first-reaction dehydrogenation zone effluent;
   (f) passing said removed second-reaction oxidation zone product stream of step (e) to a third-reaction dehydrogenation zone containing a dehydrogenation catalyst comprising an alkaline metal-promoted iron catalyst at dehydrogenation conditions to produce dehydrogenated hydrocarbons; and
   (g) withdrawing and recovering said dehydrogenated hydrocarbons, the improvement which comprises utilizing as a support precursor for said oxidation catalyst an alumina which posses an Apparent Bulk Density less than about 0.6 g/cc, a pore volume greater than about 0.5 cc/g, a pore distribution such that between about 10% and 70% of the pore volume is present in pores greater than 300 Angstroms in diameter, and which support, after peptizing and calcination thereof, possesses an Apparent Bulk density in the range of from about 0.3 to about 1.1 g/cc, a pore volume greater than about 0.2 cc/g, a pore distribution such that more than 40% of the pore volume is present in pores greater than 1500 Angstroms, a piece density in the range of from about 0.3 to about 2.0 g/cc, a surface area in the range of from about 1 to about 40 m$^2$/g, and a particle size which possesses a diameter of at least 2 mm.

2. The process of claim 1 in which said support particle comprises and extrudate which possesses a diameter in the range of from about 2 mm to about 15 mm and a length in the range of from about 2 mm to about 50 mm.

3. The process of claim 1 in which said support particle is in spherical shape which possesses a diameter in the range of from about 2.0 mm to about 20 mm.

4. The process of claim 1 in which said calcined support comprises a mixture of alpha and theta-alumina.

5. The process of claim 1 in which said calcined support comprises alpha-alumina.

6. The process of claim 1 in which said alumina precursor comprises a boehmite, pseudoboehmite, or gibbsite.

7. The process of claim 1 in which said dehydrogenation and oxidation conditions include a temperature in the range of from about 500° to about 700° C. and a pressure in the range of from about 0.1 to about 10 atmospheres.

8. The process of claim 1 in which said Group VIII noble metal is present in said oxidation catalyst in an amount in the range of from about 0.01% to about 5% by weight of said catalyst.

9. The process of claim 1 in which said Group IVA metal is present in said oxidation catalyst in an amount in the range of from about 0.01% to about 5% by weight of said catalyst.

10. The process of claim 1 in which said Group IA or IIA metal is present in said oxidation catalyst in an amount in the range of from about 0.01% to about 10% by weight of said catalyst.

11. The process of claim 1 in which said alkaline metal of said dehydrogenation catalyst is selected from the group consisting of Group IA and IIA of the Periodic Table.

12. The process of claim 1 in which said dehydrogenation catalyst contains an oxide or a sulfide of a metal selected from the group consisting of Groups IVB, VB and VIB of the Periodic Table.

13. The process of claim 1 in which said Group VIII noble metal of the Periodic Table is selected from the group consisting of platinum, palladium and rhodium.

14. The process of claim 1 in which the metal of Group IVA of the Periodic Table is selected from the group consisting of germanium, lead, and tin.

15. The process of claim 1 in which the metal of Group IA or IIA of the Periodic Table in the oxidation catalyst is selected from the group consisting of sodium, lithium, potassium, rubidium, cesium, beryllium, magnesium, calcium, francium, radium, strontium and barium.

16. The process of claim 1 in which said oxygen-containing gas is air.

17. The process of claim 1 in which said oxygen-containing gas is oxygen.

18. The process of claim 1 in which said dehydrogenatable hydrocarbon is ethylbenzene and said dehydrogenated hydrocarbon is styrene.

19. The process of claim 1 in which said dehydrogenatable hydrocarbon is p-ethyltoluene and said dehydrogenated hydrocarbon is p-methylstyrene.

* * * * *